US00PP12571P2

(12) United States Plant Patent
Slaughter et al.

(10) Patent No.: US PP12,571 P2
(45) Date of Patent: Apr. 23, 2002

(54) NECTARINE TREE—'BURNECTHREE'

(75) Inventors: John K. Slaughter, Clovis; Timothy J. Gerdts, Kingsburg, both of CA (US)

(73) Assignee: The Burchell Nursery, Inc., Oakdale, CA (US)

( * ) Notice: Subject to any disclaimer, the term of this patent is extended or adjusted under 35 U.S.C. 154(b) by 0 days.

(21) Appl. No.: 09/488,392

(22) Filed: Jan. 18, 2000

(51) Int. Cl.[7] ..... A01H 5/00
(52) U.S. Cl. ..... Plt./190

(58) Field of Search ..... Plt./190

*Primary Examiner*—Bruce R. Campell
*Assistant Examiner*—Annette H. Para
(74) *Attorney, Agent, or Firm*—Wells, St. John, Roberts, Gregory & Matkin, P.S.

(57) ABSTRACT

A new and distinctive variety of nectarine tree denominated varietally as 'Burnecthree', and which is characterized as to novelty by a date of maturity for commercial harvesting and shipment of approximately July 8 to July 15, under the ecological conditions prevailing in the San Joaquin Valley of central California.

1 Drawing Sheet

BACKGROUND OF THE NEW VARIETY

The present invention relates to a new, novel and distinct variety of nectarine tree, which has been denominated varietally as 'Burnecthree'. The 'Burnecthree' Nectarine Tree produces an exceptionally high quality nectarine which is mature for harvesting and shipment in the mid-season. Still further, another unique aspect of the 'Burnecthree' is that it yields a very firm nectarine that exhibits high eating quality as compared with the other nectarine varieties which ripen at approximately the same time of the season.

ORIGIN OF THE NEW VARIETY

The present variety of nectarine tree was derived from an ongoing program of fruit and nut tree breeding. The purpose of this program is to improve the commercial quality of deciduous fruit and nut varieties and rootstocks by creating and releasing selections of *prunus, malus* and *regia* species. To this end, we make both controlled and hybrid crosses each year in order to produce seedling populations from which improved progenies are evaluated and selected. The nectarine seedling 'Burnecthree' was originated by us in 1994, and chosen from among a population of seedlings which resulted from a controlled cross pollination of the 'Grand Diamond' Nectarine Tree (U.S. Plant Pat. No. 4,095), which was used as the pollen parent, and the 'Flame Glo' Nectarine Tree (U.S. Plant Pat. No. 8,441), which was used as the seed parent. The resulting seed from this cross pollination was planted in the spring of 1995. The new variety was selected from among seedlings growing in experimental orchards located near the city of Fowler, Calif., County of Fresno, in the central San Joaquin Valley. The Nectarine Tree 'Burnecthree' was subsequently marked and noted as having exceptional characteristics. It has been subsequently evaluated during the 1996–1999 fruiting seasons. After the 1996 season, the 'Burnecthree' Nectarine Tree was selected for advanced evaluation and repropagation.

ASEXUAL REPRODUCTION OF THE NEW VARIETY

Scion wood from the original seedling of the Nectarine Tree, 'Burnecthree' was collected and grafted in the evaluation plot of the experimental orchard previously described onto two different and existing Nemared_(unpatented) rootstocks in February of 1997. Fruit from the resulting propagation has been subsequently evaluated for the 1998 and 1999 fruiting seasons. This latter evaluation clearly demonstrated that the repropagated trees were true to the characteristics of the original seedling in all observable respects.

SUMMARY OF THE NEW VARIETY

The 'Burnecthree' Nectarine Tree is characterized as to novelty by producing fruit which have a mid-season ripening date, and which is further of high quality, firm, and has an attractive exterior coloration. In this regard, the present variety of nectarine tree bears clingstone fruit which are ripe for commercial harvesting and shipment during approximately July 8 to July 15. These harvesting dates are approximately one week later than the harvest dates of the commercial freestone nectarine variety 'Summer Grand' Nectarine Tree (U.S. Plant Pat. No. 2,879). The present variety distinguishes itself from the Summer Grand Nectarine Tree, however, by producing fruit having a brighter and more extensive exterior coloration, improved flavor, and additionally, has a firmer flesh. Further, the 'Burnecthree' Nectarine Tree distinguishes itself from the Summer Grand Nectarine Tree in that the fruit of the 'Burnecthree' Nectarine Tree has an extended shelf life, after it is harvested, in relative comparison to the fruit of the Summer Grand Nectarine Tree. The subject variety differs from the 'Grand Diamond' in that 'Burnecthree' is a clingstone fruit and has much more luster in its external finish than does the fruit of the 'Grand Diamond'. The subject variety also differs from the 'Flameglo' nectarine in that the 'Burnecthree' fruit is generally larger and does not have a predominate pistil point which consistently appears on the fruit of the 'Flameglo'.

BRIEF DESCRIPTION OF THE DRAWING

The accompanying drawing is a color photograph of a characteristic twig bearing typical leaves; several leaves showing both the dorsal and ventral coloration thereof; and several mature fruit showing their external coloration sufficiently matured for harvesting and shipment. Additionally, one fruit of the subject variety is dissected in the equatorial or cheek plane to illustrate the flesh and stone characteristics.

DETAILED DESCRIPTION

Referring more specifically to the pomological details of this new and distinct variety of nectarine tree, the following has been observed under the ecological conditions prevailing at the orchards previously described, and which are located near the town of Fowler, county of Fresno, state of California. Observations were made of the original seedling tree on its own root during the growing years of 1996–1999. All major color code designations are by reference to The R.H.S. Colour Chart (1995 Third Edition) provided by The Royal Horticultural Society of Great Britain.

Tree:

*Size.*—Generally — Average to above average as compared to other common nectarine cultivars.

*Productivity.*—Productivity with respect to pounds per acre is not available. This trait is highly dependent on cultural practices and is not distinctive of the variety.

*Form.*—The original seedling was trained in a central leader configuration with a moderate spread in the crown of the tree. The tree is considered upright to upright spreading in form.

*Height.*—The original seedling had a height dimension of 3.86 m at the end of the 1999 growing season.

*Width.*—The original seedling tree had a width of 2.1 m at the end of the 1999 growing season.

*Current season growth.*—The current season growth for the new variety was approximately 0.79–1.0 m.

*Regularity of bearing.*—Regular, and considered hardy under typical Central San Joaquin Valley climatic conditions.

Trunk:

*Thickness.*—Approximately 61.2 mm in diameter when measured at a distance of approximately 15.24 cm above the soil level, at the end of the 1999 growing season.

*Bark texture.*—Considered moderately rough with numerous folds of papery scarf skin being present.

*Lenticels.*—Numerous flat, oval lenticels are present. The lenticels range in size from approximately 3.0 to 7.0 millimeters in width and from approximately 1 to 2 millimeters in height.

*Lenticels color.*—Tan Brown (RHS Greyed-Orange Group 173 D).

*Bark coloration.*—Variable, but it is generally considered to be a grey-brown (RHS Greyed-Orange Group 174 A).

Branches:

*Size.*—Considered medium for the variety.

*Diameter.*—The branches have a diameter of 38.1 mm when measured during the 3$^{rd}$ year after grafting.

*Surface texture.*—Average, and appearing furrowed on wood which is several years old.

*Crotch angles.*—Variable between about 41.0° to 46.0° from the horizontal axis for scaffold limbs. This is not distinctive of the variety however.

*Current season shoots.*—Surface Texture — Substantially glabrous.

*Internode length.*—Approximately 2.2 to 2.4 cm.

*Color of mature branches.*—Medium brown, (RHS Greyed Orange Group 175 C to 177 B).

*Current season shoots.*—Color — Light green, (RHS Yellow Green Group 144 C), with some reddish-brown coloration appearing on exposed exterior shoots (RHS Greyed Red Group 181 B). The color of the new shoot tips is considered a bright and shiny green (RHS Green Group 143 B).

Leaves:

*Size.*—Considered average for the species. Leaf measurements have been taken from vigorous upright current season growth at approximately midshoot.

*Leaf length.*—Approximately 176 to 188 millimeters.

*Leaf width.*—Approximately 48 to 51 millimeters.

*Leaf thickness.*—Approximately 1 to 2 millimeters.

*Leaf base shape.*—Slightly oblique.

*Leaf form.*—Lanceolate.

*Leaf tip form.*—Acuminate.

*Leaf color.*—Dark green (RHS Green Group 132 C).

*Leaf texture.*—Glabrous.

*Lower surface color.*—Light green, (RHS Yellow Green Group 146 B).

*Venation.*—Pinnately net veined.

*Mid-vein.*—Color — Light yellow green, (RHS Yellow Green Group 153 B).

*Leaf margins.*—Form — Considerate crenate, and occasionally doubly crenate. Uniformity — Considered generally uniform.

*Leaf petioles.*—Size — Considered medium. Length — Approximately 6 to 9 millimeters. Diameter — Approximately 1.5 to 2 millimeters. Color — Pale green, (RHS Yellow Green Group 150 C).

*Leaf glands.*—Size — Approximately one to two millimeters in height and two to three millimeters in width. Numbers — Generally 1–2 per side. Occasionally two per side. Type — Reniform and small. Color — Greenish brown, (RHS Grey Brown Group 199 C).

*Leaf stipules.*—Size — Approximately 6 to 9 mm in length; 1.0 mm in width. Number — Typically 2 per leaf bud and up to 6 per shoot tip. Form — Lanceolate in form with a serrated margin. Color — Green (RHS 135 A) when young, but changing to a yellow-brown (RHS Greyed-Orange Group 174 A) color with advancing senescence. The stipules are considered to be early deciduous.

Flowers:

*Flower buds.*—Generally — The floral buds are considered to be medium in size (16.0 mm long and 9.0 mm wide), plump to slightly pointed in form, and slightly appressed, relative to the bearing shoot.

*Flower buds.*—Color — The bud scales are gray-brown, (approximately RHS Greyed Orange Group 177 B). The buds are considered hardy under typical central San Joaquin Valley climatic conditions.

*Hardiness.*—No winter injury has been noted during the several years of evaluation in the Central San Joaquin Valley. The current variety has not been intentionally subjected to drought or heat stress and therefore this information is not available.

*Blooming time.*—Considered slightly earlier than average in relation to other nectarine cultivars commonly growing in the Central San Joaquin Valley. Date of full bloom was observed on Mar. 4, 1998.

*Flower type.*—The variety is considered to be a showy type flower.

*Flower diameter.*—Flower diameter at full bloom is approximately 38 to 45 millimeters.

*Bloom quantity.*—Considered abundant.

*Flower bud frequency.*—Normally 1 to 2 buds appear per node, although 1 bud per node is more common.

*Petal size.*—Generally — Considered medium-large for the species. Length — Approximately 17 to 22 millimeters. Width — Approximately 16 to 20 millimeters.

*Petal shape.*—Broadly ovate.

*Petal count.*—Nearly always 5.

*Petal texture.*—Glabrous.

*Petal color.*—Light pink when young (approximately RHS Red Purple Group 69 C), and with advancing senescence changing to a very pale pink (RHS Red Purple Group 68 B). The lower portion of the flower petal is typically darker that the apical portions and exhibits a dark pink coloration (RHS Red-Purple Group 64 B).

*Petal claw.*—Form — The claw is considered truncate in shape and has a medium size when compared to other similar varieties. Length — Approximately 1.5 to 2 millimeters. Width — Approximately 1 millimeter.

*Petal margins.*—Generally — Considered variable, from nearly smooth, to moderately undulate.

*Petal apex.*—Generally — The petal apices appear slightly domed.

*Flower pedicel.*—Length — Considered medium-short, and having an average length of approximately 2.0 to 3.0 millimeters. Diameter — Considered average, approximately 2 millimeters. Color — Bright green (RHS Yellow Green Group 144 D).

*Floral nectaries.*—Color — Dull orange, to an orange-gold color (approximately RHS Greyed Orange Group 168 B). The color of the nectaries become increasingly dull and slightly darker with advancing senescence.

*Calyx.*—Surface Texture — Generally glabrous, with some slight ribbing being occasionally evident. Color — A dull red, (approximately RHS Greyed Red Group 184 A).

*Sepals.*—Surface Texture — The surface has a medium length, wooly, and gray (RHS Greyed-Purple Group 183 D) colored pubescence. Number — Generally 5 per flower. Size — Average, and ovate in form. Typically 4.0 mm wide and 6.0 mm long. Color — A dull red, (approximately RHS Greyed Red Group 178 A).

*Anthers.*—Generally — Average in size. Color — Red to reddish-orange dorsally, (approximately RHS Greyed Purple Group 187 D). Pollen production — Pollen is abundant, and has a yellow-gold color, (approximately RHS Orange 26 A).

*Filaments.*—Size — Varaible in length, approximately 14 to 16 millimeters. Color — White, (RHS Red Purple Group 69 D), and darkening with advanced maturity.

*Pistil.*—Generally — Average in size. Length — Approximately 15 to 17 millimeters, including the ovary. Color — Considered a very pale green, at mid-bloom, (approximately RHS Yellow Green Group 151 D). Surface Texture — Glabrous.

Fruit:

*Maturity when described.*—The present variety of fruit is described, as it would be found in its firm ripe condition at full commercial maturity. In this regard, the fruit of the present variety was first picked on approximately Jul. 8, 1998. The date of last pick of the same fruit in 1998 was approximately Jul. 15, 1998 under the ecological conditions prevailing in the San Joaquin Valley of Central California.

*Size.*—Generally — Medium in size, and considered moderately uniform. Average Cheek Diameter — Approximately 75 to 78 millimeters. Average Suture Diameter — Approximately 75 to 79 millimeters. Average Axial Diameter — Approximately 74 to 77 millimeters. Fruit Weight — This is highly dependent on agricultural practices, and therefore is not distinctive of the present variety.

*Fruit form.*—Generally — Globose in its lateral aspect. The fruit is generally uniform in symmetry and having a rounded form when viewed from the apical aspect.

*Fruit suture.*—Generally — The suture appears as a thin line, which extends from the base to the apex, and which appears slightly deeper, basally, within the stem well, and apically on both sides of the pistil point. No apparent callousing or stitching exists along the suture line.

*Suture.*—Color — The suture normally is the same color as the underlying blush, both where the orange-yellow background color, (RHS Orange Group 24 C) and the red orange color, (RHS Red Group 46 A to 46 B) occur.

*Ventral surface.*—Form — Considered uniform.

*Stem cavity.*—Size — Considered moderately for the species.

*Width.*—Approximately 19–21 millimeters.

*Length.*—Approximately 27–30 millimeters.

*Depth.*—Approximately 10 to 11 millimeters.

*Form.*—Considered narrowly oval.

*Fruit base.*—Generally — Considered truncate to slightly oblique in form, and uniform.

*Fruit apex.*—Generally — Considered depressed and usually recessed below the height of the apical shoulders.

*Fruit stem.*—Generally — Considered medium in length, approximately 9 to 10 millimeters.

*Diameter.*—Approximately 3 to 4 millimeters.

*Color.*—Generally a pale yellow-green, (approximately RHS Yellow Green Group 145 B).

*Fruit skin.*—Generally — Considered average in thickness. Surface Texture — The variety has a very glabrous surface. Skin Acidity — Considered neutral.

*Tenacious to flesh.*—Yes at commercial maturity.

*Tendency to crack.*—Not observed.

*Skin color.*—Generally — Variable, with approximately 80% to 90% of the fruit surface covered with a brilliant crimson red blush.

*Blush color.*—The blush color is generally more prevalent apically. This red blush color ranges from a dark red, (RHS Red Group 46 A and B) to an orange red, (RHS Orange-Red Group 33 B), with many degrees of shading and blending occurring between these colorations.

*Skin ground color.*—This is generally present in variable percentages covering approximately 10% to 20% of the fruit's surface, which has a yellow-golden color, (RHS Yellow Orange Group 22 A to 24 C).

*Flesh color.*—Generally — Considered varaible, having a yellow-orange color in a range, (RHS Yellow Orange Group 21 C to 21 A).

*Flesh fibers.*—Generally — Present, numerous, fine and light colored. These fibers are present throughout the flesh.

*Stone cavity.*—Red, (approximately RHS Red Group 45 B) to a yellow orange, (approximately RHS Yellow Orange Group 18 B).

*Flesh texture.*—Generally — The flesh is considered firm and fine at commercial maturity. The flesh texture is considered non-melting.

*Ripening.*—Generally — The fruit of the present variety ripens evenly.

*Flavor.*—Considered very sweet and having moderate acidity. The flavor is considered both pleasant and well balanced.

*Aroma.*—Pleasant and abundant.

*Eating quality.*—Generally — Considered very good to excellent and well above average when compared to other common commercial varieties.

Stone:

*Attachment.*—Generally — The stone is considered to be a clingstone at full commercial maturity.

*Stone size.*—Generally — Considered medium for the species.

*Length.*—Approximately 32 to 35 millimeters.

*Width.*—Approximately 24 to 27 millimeters.

*Thickness.*—Approximately 23 to 24 millimeters.

*Fibers.*—Generally — A few medium length fibers are attached along the entire surface area of the stone.

*Stone form.*—Generally — The stone is considered rounded to slightly oval.

*Stone base.*—The stone is generally considered truncate.

*Base angle.*—The base angle of the stone is variable, but occasionally is considered oblique to the stone axis.

*Hilum.*—Generally — Considered medium in size, and relatively well defined. The hilum is approximately 5 to 7 millimeters long and approximately 3 to 4 millimeters wide. Form — Considered oval.

*Apex.*—Shape — The stone apex is raised and has an acute tip.

*Stone shape.*—Considered variable. The stone is normally equal, although occasionally it may appear nearly unequal.

*Stone surface.*—Surface Texture — Generally, considered medium in roughness and exhibits substantial pitting laterally. Substantial grooving is apparent over the apical shoulders. Surface pitting is prominent, generally, and is present more frequently basally. Ridges — Numerous fine ridges are present basally and converge towards the base of the stone.

*Ventral edge.*—Width — Considered medium in size, and prominent, and having a dimension of approximately 5 to 7 millimeters when measured at mid-suture. The wings are most prominent over the basal area.

*Dorsal edge.*—Full, heavily grooved, and having jagged edges. The dorsal edge is moderately eroded over the apical shoulder.

*Stone color.*—The color of the dry stone is approximately a light to medium brown, (RHS Orange Red Group 34 C).

*Tendency to split.*—No splitting noted.

*Kernel.*—Form — Oval. Length — Approximately 16.0–19.0 mm. Width — Approximately 12.0–14.0 mm. Thickness — Approximately 5.0–6.0 mm. Pellicle — Pubescent. Color — RHS Greyed-Orange Group 172 B.

*Use.*—The subject nectarine variety Burnecthree is considered to be a nectarine of mid-season maturity, which produces a very firm, highly attractive colored fruit which is useful for both local, long distance, and export shipping.

*Keeping quality.*—Fruit has stored well up to 20 days after harvest at temperatures of about 1° C.

*Resistance to insects and disease.*—No particular susceptibilities were noted.

*Shipping quality.*—Well above average.

Although this new variety of nectarine tree possesses the described characteristics noted above, as a result of the growing conditions prevailing in the central part of the San Joaquin Valley of central California, it is to be understood that variations of the usual magnitude and characteristics incident to changes in growing conditions, fertilization and pruning and pest control are to be expected.

Having thus described and illustrated our new variety of nectarine tree, what we claim as new and desire to secure by Plant Letters Patent is:

1. A new and distinct variety of nectarine tree substantially as illustrated and described, and which is characterized as to novelty by producing an attractively colored clingstone nectarine which is sufficiently matured for harvesting and shipment July 8 to July 15 under the prevailing ecological conditions in the San Joaquin Valley of central California.

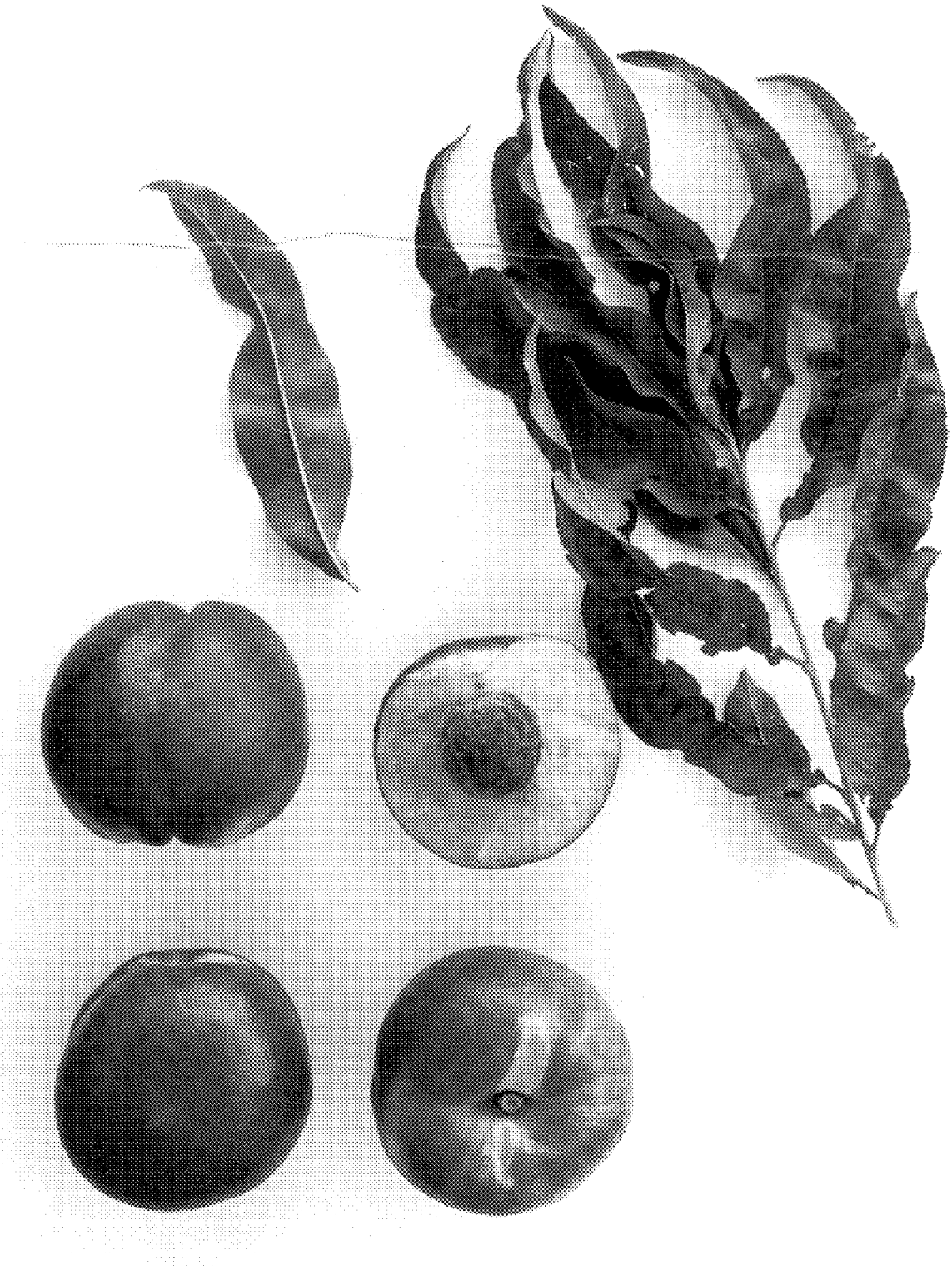

* * * * *